United States Patent [19]

Kennette et al.

[11] 4,035,217

[45] July 12, 1977

[54] METHOD OF MANUFACTURING ABSORBENT FACING MATERIALS

[75] Inventors: John Wilson Kennette, Somerville; Irving Stanley Ness, Princeton, both of N.J.

[73] Assignee: Johnson & Johnson, New Brunswick, N.J.

[21] Appl. No.: 583,932

[22] Filed: June 5, 1975

Related U.S. Application Data

[60] Continuation-in-part of Ser. No. 431,271, Jan. 7, 1974, abandoned, which is a division of Ser. No. 363,459, May 24, 1973, Pat. No. 3,828,783.

[51] Int. Cl.² .................. B32B 21/10; A61F 13/16; B32B 5/16
[52] U.S. Cl. ............................... 156/279; 128/284; 156/291; 156/305; 156/324; 428/128; 428/198; 428/284; 428/288; 428/290
[58] Field of Search ............... 156/62.2, 62.4, 279, 156/291, 305, 324; 19/161 P; 128/284, 287, 290 R, 290 W, 296; 162/184, 142, 147, 168 R, 164 R; 428/172, 284, 198, 288, 280, 289, 290, 128

[56] References Cited

U.S. PATENT DOCUMENTS

| 3,720,562 | 3/1973 | Drelich | 156/291 |
| 3,726,750 | 4/1973 | Stillings | 156/62.4 |
| 3,747,161 | 7/1973 | Kalwaites | 19/161 P |
| 3,764,451 | 10/1973 | Dunning | 156/62.2 |
| 3,770,534 | 11/1973 | Anselrode | 156/279 |

Primary Examiner—William A. Powell
Assistant Examiner—Thomas Bokan
Attorney, Agent, or Firm—Charles J. Metz

[57] ABSTRACT

An absorbent facing material comprising 10 to 30% cellulosic, staple length, textile fibers, 60 to 80% of fluff wood pulp, and 5 to 25% of a resin binder material. The cellulosic fibers are substantially only on one surface of the material and the wood pulp substantially only on the opposite surface. The binder is distributed in a predetermined pattern with the surface containing the cellulosic fibers having a higher concentration of binder than the surface containing the wood pulp fibers.

1 Claim, 5 Drawing Figures

U.S. Patent   July 12, 1977   4,035,217
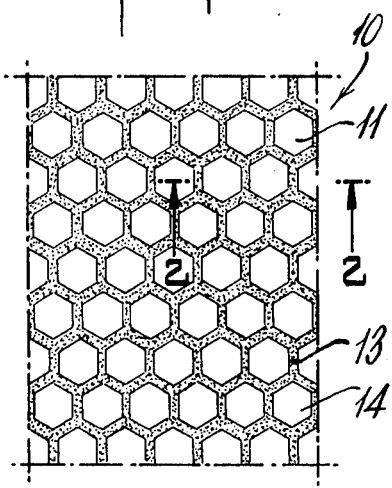
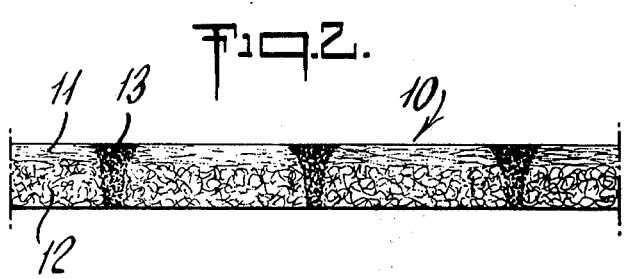
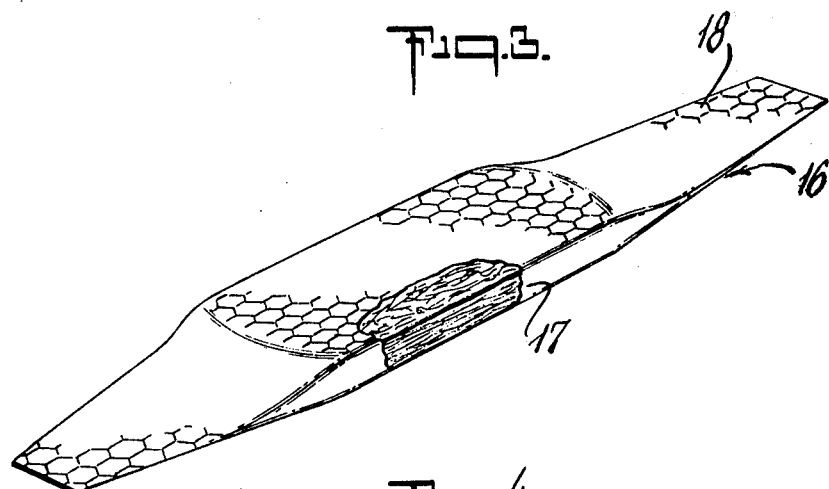
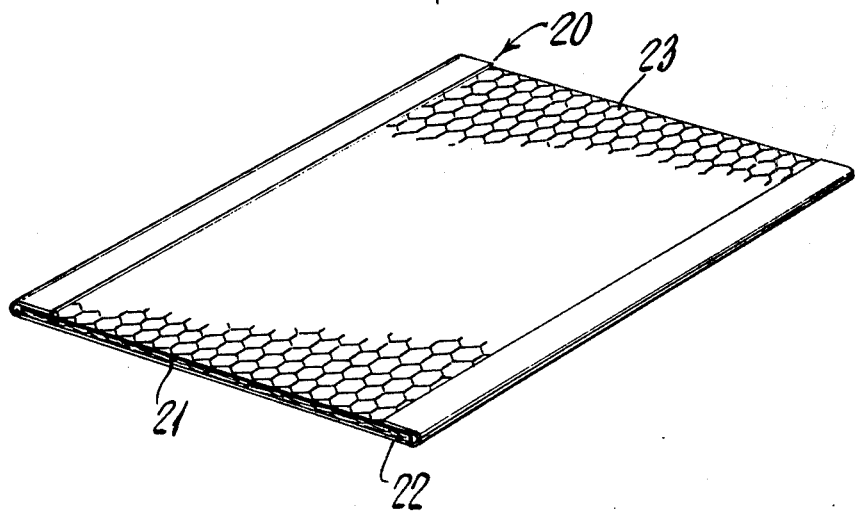

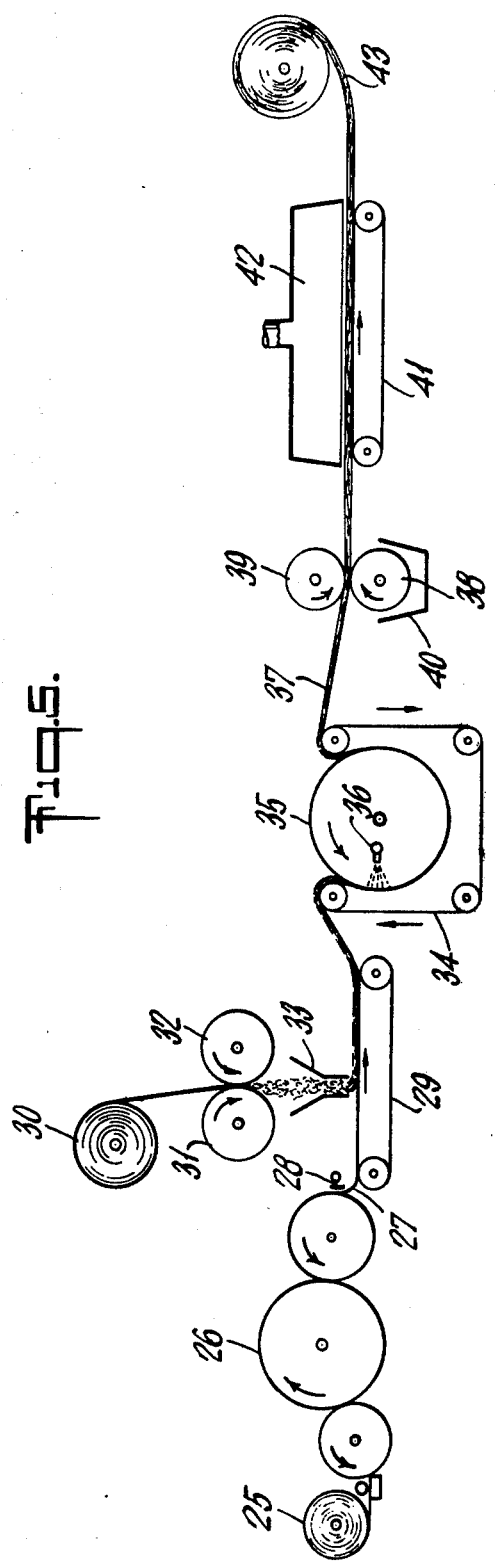

METHOD OF MANUFACTURING ABSORBENT FACING MATERIALS

This application is a continuation-in-part of application Ser. No. 431,271 filed Jan. 7,1974, now abandoned, which is a division of application Ser. No. 363,459 filed May 24, 2973, now U.S. Pat. No. 3,828,783.

the present invention is directed to a new nonwoven fabric and more particularly to a highly absorbent, stabilized fabric suitable for use as the facing for absorbent products.

Nonwoven fabrics have gained considerable use as the facing or outer layer or absorbent products such as underpads, diapers, sanitary napkins and the like. The facing material is primarily used to contain the absorbent core and in some instances provide other properties in the final product. Such properties may be maintaining a dry surface when the product is in use, improving the wicking characteristics and distribution of the fluid to be absorbed within the product to make more efficient use of the absorbent core, abrasion resistance, and so forth.

We have discovered a new facing material for use on absorbent products. Our new facing material has excellent softness and good wicking and fluid distribution properties. Furthermore our new facing material is very soft, highly absorbent, abrasion resistant, and improves the stability of the entire product in that it has one surface which stabilizes and holds the absorbent core in place during use.

In accordance with the present invention our new absorbent facing material weighs at least one ounce per square yard and comprises 10 to 30% of cellulosic, staple length, textile fibers, 60 to 80% of fluffed wood pulp and 5 to 25% of an adhesive resin binder. The facing material has the cellulosic fibers substantially only on one surface of the material and the wood pulp substantially only on the other surface of the material. The resin binder is distributed in a pattern over the material with the concentration of resin being greater on the cellulosic fiber surface than it is on the wood pulp surface of the material.

Our new facing material is manufactured by forming a web of cellulosic textile length fibers and uniformly depositing wood pulp on one side of the textile fiber web to form a fiberwood pulp laminate. The laminate is confined between a pair of moving surfaces and while confined the laminate is thoroughly wetted with water. A resin binder is deposited on the wet laminate with the resin being applied to the web side of the laminate in a pattern. The laminate with the resin thereon is dried to remove the water and cure the binder and produce the absorbent facing material.

The facing material is used in combination with an absorbent core wherein the absorbent core may be fluffed wood pulp or absorbent creped tissue or similar highly absorbent materials. The facing material may be used to wrap the entire core or it may be used on one surface of the core with the other surface of the core being covered with a waterproof film such as polyethylene or the like. In use the facing material is applied to the absorbent core with the wood pulp surface in contact with the core so that the cellulosic textile fiber-rich surface is the exposed surface of the final product. This configuration produces an absorbent product having a smooth, soft surface which is abrasion resistant.

The facing also aids in uniformly wicking and distributing the fluid being absorbed into the core. Furthermore this configuration is highly absorbent and the wood pulp surface which has a higher coefficient of friction than the cellulosic textile fiber surface contacts the absorbent core and stabilizes and holds the core in place during use.

The invention will more fully described when taken in conjunction with the accompanying drawings wherein: FIG. 1 is a plan view of the new absorbent facing material of the present invention.

FIG. 2 is a cross-sectional view taken along lines 2—2 of FIG. 1.

FIG. 3 is a sanitary napkin which utilizes the new absorbent facing material of the present invention.

FIG. 4 is a disposable diaper which uses the new absorbent facing material of the present invention.

FIG. 5 is a schematic flow sheet of apparatus useful in carrying out the method of the present invention.

Referring to the drawings in FIGS. 1 and 2 there is depicted an absorbent facing material of the present invention. The absorbent facing material 10 comprises an upper or top layer 11 of cellulosic, textile, staple length, fibers and a bottom or lower layer 12 of fluffed wood pulp. A resin binder 13 is distributed over the textile fiber layer in a pattern so as to form substantially unbonded hexagon areas 14 in the layer. As is more clearly seen in FIG. 2 the concentration of binder is greater in the textile fiber layer 11 than it is in the remainder of the facing material.

The cellulosic fibers used may be any of the natural or artificial cellulosic fibers; such as, cotton, rayon, and the like. The cellulosic fibers must have a length of at least ½ inch up to 2½ inches or more. The minimum fiber length is required in order to carry the laminate through the process for producing the final facing material and to provide strength in the final product.

The wood pulp may be any of the known wood pulps such as Kraft pulps, sulfite pulp, and the like. The pulp is ground into a fine, highly absorbent, particulate configuration.

The binders used to hold the laminate together may be any of the well known polymer resin binders used in bonding nonwoven fabrics; for example, self cross-linking acrylate resins, polyvinyl chloride resins, polyvinyl acetate resins and the like. The binder is applied in a predetermined pattern to the surface containing the cellulosic textile fibers. The pattern may have a configuration of hexagons as shown, or circles or dots or other configurations as long as there are substantially unbonded fiber areas on the cellulosic textile fiber surface to aid in the wicking and distribution of the fluid to be absorbed.

To produce a facing material having the desired softness, abrasion resistance, and absorbency properties and to also stabilize the absorbent core during use of the final product, the facing should weigh at least one ounce per square yard. Lighter weight materials will not produce either the desired absorbency or the desired stabilization of the core.

In FIG. 3 there is shown a sanitary napkin 16 which utilizes the absorbent facing material of the present invention as the cover of the napkin. The napkin comprises an absorbent core 17 which may be multiplicity of plies of crepe tissue, a thick layer of fluffed wood pulp or similar material that is highly absorbent. The core is wrapped with the facing material 18 of the present invention with the surface containing the high concentration of wood pulp fibers in contact with the core to stabilize and hold the core in place.

In FIG. 4 there is shown a disposable diaper 20 utilizing the facing material of the present invention. The diaper comprises an absorbent core 21 which may be either a multiplicity of plies of creped tissue or a fluffed wood pulp core. The core is backed with a water repellent or water-proof film 22 such as polyethylene film. The opposite surface of the core is covered with the facing material 23 of the present invention. The wood pulp surface of the facing material is in contact with the core to stabilize and hold the core in place during use. The cellulosic textile fiber surface forms the outer surface of the diaper and is soft, abrasion resistant, and highly absorbent.

Though sanitary napkins and disposable diapers have been depicted in FIG. 3 and 4 there are various other absorbent products with which the facing material of the present invention may be used; such as, tampons, underpads, bandages, and the like.

In FIG. 5 there is schematically depicted one form of apparatus for manufacturing the absorbent facing material of the present invention. A lap 25 of cellulosic, staple length textile fibers is fed to a standard card machine 26 and a carded fiber web 27 is removed from the card machine by a standard doffing comb 28 and placed on a moving conveyor 29. Wood pulp board 30 is passed between counter-rotating toothed rolls 31 and 32 to grind the wood pulp and deposit it through the funnel 33 onto the surface of the card web. The wood pulp is preferably ground by mechanical means such as Bauer mills, Fitz mills, manner mills and the like. The mechanically ground wood pulp is less susceptible to hydrogen bonding under pressure than, for example, beaten wood pulp. The undesirable features of hydrogen bonding will be described more fully hereinafter. The laminate of cellulosic fibers and wood pulp is confined between a continuous foraminous belt 34 and a rotatable foraminous drum 35. The belt contacts the drum about a portion of its periphery and water is sprayed with suitable nozzles 36 through the foraminous drum into the web and out through the belt to thoroughly wet out the laminate. The belt, drum and laminate move at the same linear speed. The wetted laminate 37 is passed through a pair of rotating rolls 38 and 39. The bottom roll 38 rotates in a reservoir 40 of resin binder. The roll has the desired binder pattern engraved on its surface. The roll 38 contacts the cellulosic textile fiber surface of the wet laminate and deposits the resin binder in a pattern on the laminate. The laminate with the binder thereon is placed on the conveyor 41 and passed through an oven 42 where it is dried and the binder cured. The bonded nonwoven facing material 43 is rolled up. The facing may be used in combination with various types of absorbent cores to produce the final products previously described.

The cellulosic textile fiber web may be produced by standard methods such as carding, air laying, wet laying techniques and the like. The wood pulp may be produced by any of the known grinding methods such as Bauer mills, hammer mills, and the like which grind the pulp board into finely divided particulate wood pulp material.

The fiber-pulp laminate is confined between a pair of moving foraminous surfaces and is thoroughly wetted with water. It is critical to the present invention that the pulp-fiber laminate be confined when wetted to produce integrity in the laminate. If the laminate is not confined when wetted it will lose its desired uniformity and will not produce a suitable facing material. The wetted laminate is bonded by known techniques such as printing. It is critical to the present invention that the binder be placed on the surface containing the cellulosic fibers. Adherence of wood pulp fibers to the printing roll occurs during laminate production if the binder is placed on the surface containing the wood pulp fibers. The accumulation of wood pulp fibers during print bonding necessitates unacceptable and frequent shutdown of production equipment and apparatus at a tremendous economical disadvantage. Consequently, for such a print bonding operation produced by confining the laminate between a pair of rotating rolls, one of which is a printing roll, the binder must be applied to the surface of the laminate containing the longer, cellulosic fibers.

There are other techniques of bonding a laminate of short and long fibers in which the adherence problem associated with print bonding is not experienced. Patents such as U.S. Pat. No 3,726,750 and U.S. Pat. No. 3,764,451 teach the bonding of such a laminate of fibers by effectuating hydrogen bonds to form a coherent structure. In the latter patent the supplemental adhesive can be applied to either short or long fibers since the hydrogen bonds have anchored the fibers in place eliminating a fiber pick-up problem adhesive printing. In the print bonding of the present invention no detectable hydrogen bonding occurs, thus no anchoring of fibers is achieved before printing. The criticality of depositing the binder to the surface of the laminate containing the textile length fibers becomes readily apparent when no hydrogen bonding occurs. The laminate with the binder thereon is dried to remove the water, cure the resin binder and bond the fibers and wood pulp together to form the final facing material.

The following is an illustrative example of the method of the present invention used in producing the absorbent facing material of the present invention.

EXAMPLE I

Using standard card machines a card web is produced. The web weighs approximately 200 grains per square yard and is made from 1 9/16 inch, 1½ denier viscose rayon fibers. Wood pulp board is ground utilizing a Bauer mill and the fully fluffed wood pulp is deposited on the card web. Approximately 700 grains per square yard of fluffed wood pulp is laid on the card web. The fiber-pulp laminate is confined between a rotating foraminous drum and a moving foraminous belt and is saturated with water to more than 100% by weight pick up of water. The wet laminate is passed through the nip formed by a pair of rolls. The roll contacting the textile fiber surface has a pattern of lines engraved in its surface with the lines forming a pattern of hexagons as shown in FIG. 1. The binder used is a self cross-linking acrylic resin emulsion and it is printed on the textile fiber-rich surface of the laminate. The laminate with the self cross-linking acrylic resin is heated to drive off the water and cross link the resin. Approximately 180 grains per square yard of resin is applied to the laminate. The resultant material has a higher concentration of binder on the textile fiber-rich surface than it has on the pulp-rich surface. The material is soft, strong and highly absorbent.

EXAMPLE II

A fiber-pulp laminate is produced as in Example I with the exception that the printing roll contacting the laminate deposits the binder on the surfce of the laminate containing the ground wood pulp fibers. The laminate is allowed to pass through the nip formed by the pair of rolls, and after approximately 500 yards of production there is a substantial accumulation of small wood pulp fibers on the printing roll necessitating shutdown of the equipment for roll cleaning. The laminate produced before equipment shutdown was analyzed for bonding with the determination that no hydrogen bonding occurred between the wood pulp fibers and textile length fibers. The only bonding found was adhesive bonding as a result of the adhesive print depositing process. The delay caused by the shutdown of the equipment for printing roll cleaning indicates that it is not economically feasible to print bond the laminate on the wood pulp surface in a production-type operation.

The above detailed description has been given for clearness of understanding only. No unnecessary limitations should be understood therefrom as modifications will be obvious to those skilled in the art.

What is claimed is:

1. The method of producing an absorbent nonwoven facing material weighing at least one ounce per square yard comprising: (a) forming a web of cellulosic, staple length textile fibers, said fibers having a length of at least ½ inch and said textile fibers comprising 10 to 30% by weight of the facing material; (b) uniformly depositing ground wood pulp on one side of the textile fiber web to form an entirely absorbent fiber-pulp laminate, said wood pulp comprising 60 to 80% by weight of the facing material; (c) confining both surfaces of the fiber-pulp laminate; (d) wetting the entire laminate with water while it is confined to saturate the laminate and produce integrity therein; (e) depositing a resin binder in an intermittent pattern to the surface of the laminate containing the staple length textile fibers, said binder comprising 5 to 25% by weight of the facing materials; and (f) drying the laminate with the binder thereon to remove the water and produce a highly absorbent stabilized facing material which is free of hydrogen bonding.

\* \* \* \* \*